United States Patent [19]

Miltenburger et al.

[11] Patent Number: 4,649,114
[45] Date of Patent: Mar. 10, 1987

[54] OXYGEN PERMEABLE MEMBRANE IN FERMENTER FOR OXYGEN ENRICHMENT OF BROTH

[75] Inventors: Herbert G. Miltenburger, Darmstadt; Sigfried Hessberg, Melsungen, both of Fed. Rep. of Germany

[73] Assignee: Intermedicat GmbH, Emmenbrücke, Switzerland

[21] Appl. No.: 446,644

[22] Filed: Dec. 3, 1982

Related U.S. Application Data

[63] Continuation of Ser. No. 185,668, Sep. 10, 1980.

[30] Foreign Application Priority Data

Oct. 5, 1979 [DE] Fed. Rep. of Germany ....... 2940446

[51] Int. Cl.$^4$ .................. C12N 5/00; C12N 5/02; C12M 3/00; C12M 3/02; C12M 1/06; B01D 13/00; B01D 29/42; B01D 29/48
[52] U.S. Cl. .................... 435/240; 435/241; 435/284; 435/286; 435/315; 210/220; 210/321.1; 210/433.2; 210/497.1
[58] Field of Search .............. 435/240, 241, 280, 284, 435/285, 286, 287, 313, 315, 2, 314; 422/48; 210/497.1, 433.2, 220, 150, 321.1, 322.2; 261/93, 122

[56] References Cited

U.S. PATENT DOCUMENTS

| | | | |
|---|---|---|---|
| 2,522,947 | 9/1950 | Hatch et al. | 435/314 |
| 3,850,748 | 11/1974 | Cook et al. | 435/241 |
| 3,927,981 | 12/1975 | Viannay et al. | 435/284 |
| 3,997,396 | 12/1976 | Delente | 435/240 |
| 4,242,460 | 12/1980 | Chick et al. | 435/284 |
| 4,259,449 | 3/1981 | Katinger et al. | 435/241 |
| 4,391,912 | 7/1983 | Yoshida et al. | 435/241 |
| 4,416,993 | 11/1983 | McKeown | 435/313 |
| 4,537,860 | 8/1985 | Tolbert et al. | 435/313 |

FOREIGN PATENT DOCUMENTS 1530705 11/1978 United Kingdom .

OTHER PUBLICATIONS

Jakoby, W. B. & Pastan, I. H., "Cell Culture", *Methods in Enzymology*, vol. 58; Academic Press, 1979; pp. 450-455.

Primary Examiner—Thomas G. Wiseman
Assistant Examiner—Elizabeth C. Weimar
Attorney, Agent, or Firm—Marshall, O'Toole, Gerstein, Murray & Bicknell

[57] ABSTRACT

The growth of animal cells in a fermenter is promoted by enriching the liquid nutrient medium or broth with oxygen diffused into the liquid through a permeable membrane, such as one made of silicone rubber or polytetrafluoroethylene (Teflon). Superior cell growth in larger volumes is achieved by feeding in the oxygen in this way instead of bubbling it in.

16 Claims, 2 Drawing Figures

OXYGEN PERMEABLE MEMBRANE IN FERMENTER FOR OXYGEN ENRICHMENT OF BROTH

This is a continuation, of application Ser. No. 185,668, filed Sept. 10, 1980.

This invention is concerned with a method and apparatus for propagating animal cells in culture suspension or monolayer culture in a fermentation vessel.

BACKGROUND OF THE INVENTION

In the last few years or so, research projects have been started directed to the production of viruses which, perhaps, can be used as biological insecticides because of their insect specie's specific activity. The production of viruses, active against specific insects, by culture propagation would permit the manufacture at any time under controlled and reproducible conditions of standardized virus preparations for use in pest control. However, the mass production of viruses active against insects requires that large amounts of insect cells be produced. This is because the insect cells are used as a necessary substrate for growing the viruses.

The propagation or multiplication of insect cells, as well as cells of vertebrae animals, in culture suspensions can be effected in shaken containers, such as the roller flasks, spinner flasks, or similar containers. In most cases, however, mass production is limited by (1) the size of the containers, which must be handled manually and (2) the oxygen partial pressure in the culture liquid nutrient medium which becomes relatively poorer with increasing culture medium volume. Usually, the air over a culture medium in a closed container is only sufficient for a limited time to replenish the oxygen consumed by the cells multiplying in the culture medium. The resulting oxygen depletion in the culture medium causes a slow down in the multiplication of cells and increased cell mortality. Because of this, as well as for the mechanical circulation of the culture medium which takes place, it has become necessary and practical to blow sterile, filtered air, in the form of finely distributed air bubbles, into the larger volumes of culture medium. In this way, the oxygen content of the culture medium is enriched.

The bubbling of germ free air into the culture medium, as currently practiced in the fermentation art to increase oxygen diffusion, is unsatisfactory for several reasons. In this method, air bubbles out of one or more openings, below the liquid level, in an air supply pipe and the bubbles rise to the surface. As the number of bubbles formed from one liter of air increases, so does the airliquid phase interface area. However, the size of the bubbles and the number of bubbles can only be varied within limits. If the openings, and thus the bubbles, are too big, they may unite before reaching the liquid surface. If the openings are made very small to generate many small bubbles, there is a danger that the openings will become plugged shut or reduced in size. Besides, the manufacture of many very small openings presents a technical difficulty.

The factors discussed above lead to a compromise in which medium sized bubbles of medium number are produced which, as a consequence, leads to an unsatisfactory phase interface area.

The phase interface area is afterwards brought to the required size by dividing the bubbles by means of a stirring apparatus and distributing them throughout the volume of culture solution in the fermenter. The pressure and pulling forces (shearing stress and tangential strain) involved in this often may damage animal cells so much that they may die.

Furthermore, additional shearing stress occurs when the gas bubbles break at the interface area (culture liquid/gas area). These forces, as well, damage the cells so that the ratio of intact cells to damaged and dead cells becomes less and less favorable although the total number may still increase.

In case it becomes necessary to increase the air (oxygen) supply by increasing the number of air bubbles, the number of damaged and dying cells increases, which is not only contrary to the desired aim of cell multiplication, but also leads increasingly to the accumulation of toxic cell decay products. These toxic products can additionally hamper cell production.

Prior to now the growth of animal cells in containers with a volume larger than three liters was hampered by the problem of oxygen supply. Regardless of whether the cells are suspended in a culture solution in the fermenter or whether they grow on surfaces in the fermenter container, after a certain ratio A/V, the growth becomes stagnant (wherein A=the area for the oxygen diffusion from the gaseous phase into the dissolved phase and V=the fermentation volume). Measurements in spinner containers of several liters showed that the $O_2$ content in a 3 liter or larger volume of nutrient medium could not be maintained, even by increased blowingin of air, on a level necessary for normally multiplying cells.

If the surface on which animal cells of certain cell groups preferably grow is artificially increased by filling the fermenter with small synthetic balls, which then are fluidized or suspended in the culture solution, the problems become even worse when air is blown in and the solution is stirred because then the balls bump against the stirring vanes and/or against one another so that damaging shearing forces and foam formation occur.

Culture liquids generally contain minimum amounts of calf-serum or other albumen-containing nutrients which promote excessive foaming when air is bubbled in. This can extremely hamper and inhibit the process.

Although stabilization of the pH value, the culture medium temperature, and the nutrient quality (by adding fresh nutrients) are important, the factor limiting the maximum volume of the fermentation vessel or container is the amount of oxygen dissolved in the nutrient medium.

It should also be emphasized that while mechanical rotation of a spinner container has to be accomplished by means of a standardized agitating apparatus, such as at 70 revolutions per minute, the mechanical rotation does not abolish oxygen depletion in the nutrient medium containing spaces.

THE INVENTION

An object of the invention is to provide an adequate supply of oxygen to cells being propagated in a liquid nutrient medium without bubbling or blowing in air, to thereby avoid the inherent disadvantages described above.

The invention also has as an object maintaining the necessary micro-mixture and macro-mixture of the fermenter liquid culture nutrient medium. This means that each volume from the liter scale to the microliter scale will contain essentially the same amounts of cells, nutrients and oxygen. Micro-mixing pertains to mixing in an area of 1 to 10 cell diameters, while macro-mixing means mixing of the entire liquid volume in the container.

According to one aspect of the subject invention there is provided an improved fermentation vessel for propagating animal cells in suspension cultures and monolayer cultures in which oxygen must be supplied to the cells in a liquid nutrient medium in the vessel for cell metabolism and multiplication, with the improvement comprising a permeable membrane, in the fermentation vessel, through which oxygen can diffuse directly into the liquid nutrient medium containing the cells.

According to a second aspect of the invention, there is provided an improved method of supplying oxygen to animal cells growing in suspension cultures and monolayer cultures in a fermentation vessel containing a liquid nutrient medium, comprising passing the oxygen through a permeable membrane in the vessel so that it diffuses directly into the liquid medium and thereby enriches it for the benefit of cell multiplication.

It was found, surprisingly, according to the invention that all of the oxygen needed for propagating animal cells in culture suspensions, or monolayer cultures, in fermentation vessels can be supplied by having the oxygen pass through a permeable membrane into the liquid. No additional supply of oxygen is needed and, in particular, the bubbling in of air is unnecessary and, thus, the disadvantages associated with that method are avoided. The method of the invention avoids the shearing forces caused by bubbling in a stream of air or oxygen, eliminates or substantially reduces foam formation, and avoids the prior art problem of correctly sizing the holes through which the air bubbled.

A very important advantage of the invention is that now, for the first time, propagation of animal cells, and particularly insect cells, is possible in culture suspensions and monolayer cultures in fermentation vessels in much larger volumes than was previously possible or customary. Thus, because of the invention is to possible to produce or ferment culture suspensions of ten liters or more with the cells multiplying at a maximum rate. Fermentation volumes can now be produced of 15 to 20 liters or more, which were not previously possible, and volumes of 50 and even 100 liters are not considered impossible.

The material used for the permeable membrane must be one which permits an adequate amount of oxygen to pass through without bubbling. However, the material selected should also be one on which the cells do not grow, or grow only slightly, for otherwise passage of oxygen through the membrane would be impaired and flow possibly reduced thereby leading to an insufficient, or undesirably low, oxygen supply in the liquid medium.

Permeable membranes useful in the invention can be made of any synthetic inert solid polymeric material. Particularly useful are membranes made of silicone rubber, laminated silicone rubber products, and polytetrafluoroethylene (Teflon). Other synthetic polymers can be used provided the animal cells do not adhere to or grow on them. Silicone foil and silicone tubes provide a surface on which the cells do not adhere, or adhere to it only with great difficulty. Therefore, synthetic silicone polymers are preferred. Regardless of the material use, the membrane should be thick enough to provide the necessary mechanical strength but thin enough to permit oxygen to pass through readily. The membrane must, of course, prevent reverse flow through it of liquid from the fermenting broth.

The permeable membrane positioned in the fermentation vessel can have any suitable size or geometric shape but one must be selected so that there is sufficient oxygen diffusion to supply the amount needed for cell metabolism. In addiiton, the permeable membrane size and shape should not interfere with cell propagation in the fermentation vessel. Those skilled in the art will be able to adapt these features, and the material of which the membrane is made, to the customary bio-technological requirements. While the permeable membrane can, itself, completely enclose a space or volume and thus constitute a hollow member, such as when in the form of a tube, sphere or closed pouch, it is also within the scope of the invention to employ a membrane which constitutes only a portion of a chamber wall or surface surrounding a space. In all instances, however, a gas supply conduit means is provided to feed an oxygen-containing gas under pressure so that it can pass from one side of the membrane, through it, and into the liquid nutrient medium on the other side. The gas supply conduit means can comprise a tube extending from outside to inside of the fermentation vessel. In addition, a gas withdrawal conduit means can be included extending from inside to outside of the fermentation vessel. Both conduit tubes should, of course, communicate with a space on the same side of the membrane or with a common chamber or volume wholly or partially defined by the membrane.

A tube or hose, having a wall about 0.6 to 1.2 mm thick and preferably about 1.0 mm thick, wound around a suitable support in the fermentation vessel is particularly useful. The support, for example, can be a heat exchanger such as is customarily used in a fermentation vessel to keep the nutrient medium and culture broth at optimum temperature.

Representative oxygen sources for the fermentation are air, a mixture of air and oxygen, or a mixture of oxygen and nitrogen.

The permeable membrane used for supplying oxygen to the culture growing in the nutrient medium also serves as a filter to remove any microorganisms in the oxygen gas supply stream, particularly when air is used, and keeps them out of the culture broth. This is a distinct advantage since all of the oxygen can be supplied through the membrane.

It should be obvious that, when the fermentation process is carried out according to the invention, the entire apparatus and the nutrient medium used must be sterile.

Providing oxygen by means of a permeable membrane according to the invention results in basically improved environmental conditions for cell culture so it is expected that improved cell multiplication rates will be obtained with a wide variety of vertebrae and non-vertebrae culture suspensions and monolayer cultures.

Vertebrae cell lines of primary importance for propagation according to the invention are those which are used in the mass production of biological products such as immunity factors, hormones, enzymes, anti-viral agents, virus preparations, and vaccines. These include the Psylla (plant lice) cell lines BHK 21, NAMALWA and 1301 cell line (from the leukemia line CCRF-CEMT).

DETAILED DESCRIPTION OF THE INVENTION

The same numbers will be used to identify the same or similar elements in the various views of the drawings.

Figure 1:
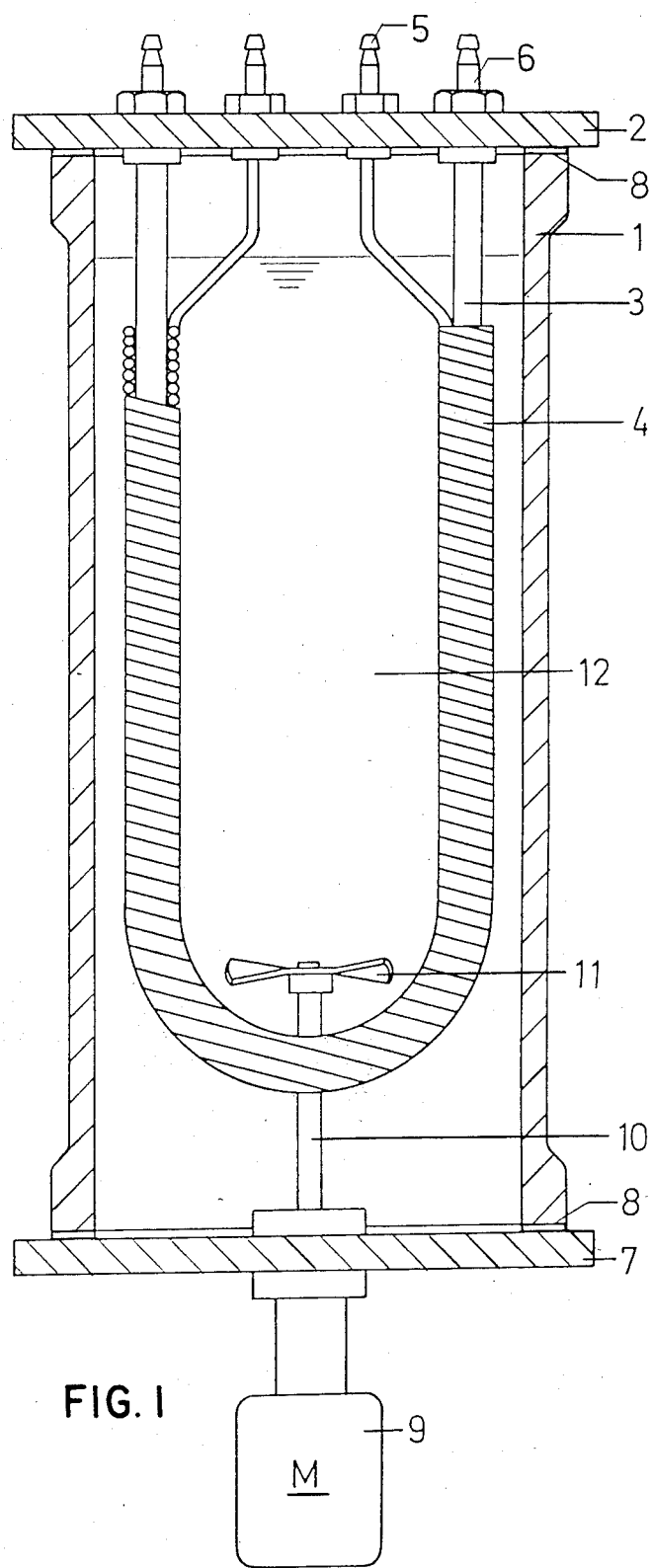
FIG. 1 is a vertical sectional view through a fermentation vessel particularly useful for cultivating animal cells suspended in a nutrient media and shows one form of permeable membrane.

With reference to FIG. 1, the fermentation vessel comprises a glass tube 1, circular in horizontal section, of borosilicate glass, a bottom 7 and a cover 2 of high quality steel. The bottom 7 and cover 2 are joined liquid and air tight to glass tube 1 by sealing rings 8. A U-shaped steel heat exchanger tube 3 penetrates, and is suspended by, cover 2. A tube 4 of silicone rubber is wound around that portion of the heat exchanger tube 3 which will normally be submerged in the liquid contents in the fermentation vessel. The wall thickness of tube 4 will usually be in the range of about 0.6 to 1.2 mm and will vary about ±0.05 mm. A wall thickness of about 1.0 mm is usually preferred. The spirals of tube 4 are not placed tightly together and desirably are spaced slightly apart. The ends of tube 4 are connected to fittings 5 which penetrate cover 2. Compressed air is supplied to tube 4 by the fittings 5. A heat exchange fluid, generally a liquid, is supplied to, and removed from, the heat exchanger tube 3 by means of fittings 6.

Motor 9 drives shaft 10 which penetrates the bottom 7. Shaft 10 contains propeller 11 inside of the fermentation vessel. Propeller 11 rotates at about 60 RPM and, by its design and low speed, assures gentle micro-mixing of the vessel contents 12. Micro-mixing is effected by the turbulent action at and adjacent to the spirally wound silicone tube 4. The oxygen, which penetrates through the wall of tube 4 and diffuses into the liquid, is predistributed by means of this micro-mixing and then it is distributed through out the vessel contents by the propeller induced circulation. The turbulence caused by gas flowing out of the spiral tube 4, and the entire liquid flow itself, assures even distribution of the nutrients and growing cells throughout the fermenting liquid volume.

Figure 2:
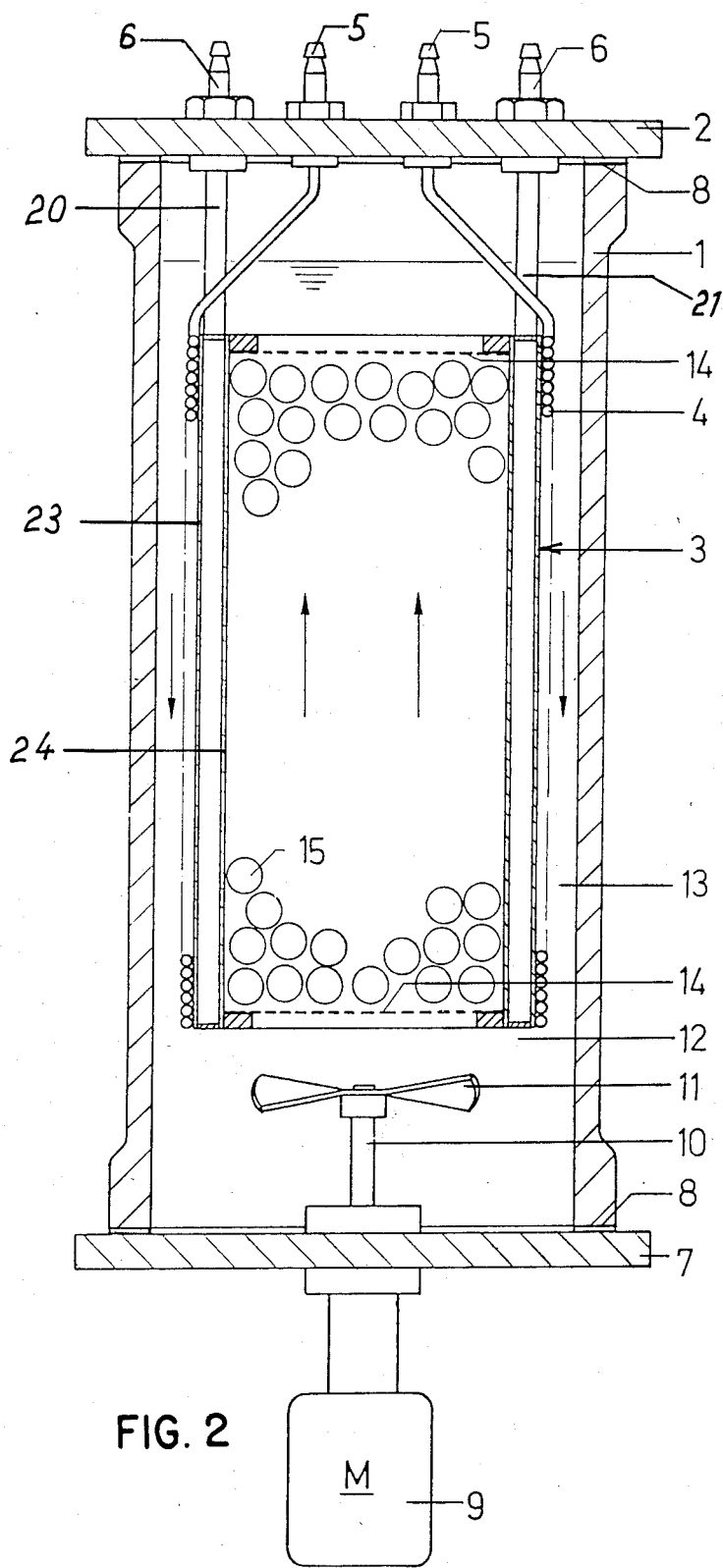
FIG. 2 is a vertical sectional view through a fermentation vessel for cultivating vertebrae cells in suspended culture as well as in monolayer culture.

With reference to the embodiment illustrated by FIG. 2, the fermentation vessel comprises a glass cylinder 1, circular in horizontal section, made of borosilicate glass. The cylinder 1 is closed by a bottom 7 and a cover 2 of high quality steel. A sealing ring 8 is positioned between the bottom 7 and the lower end of cylinder 1. Similarly, a sealing ring 8 is positioned between the cover 2 and the upper end of cylinder 1.

A heat exchanger 3 is supported by pipes 20 and 21 to cover 2. The upper ends of the pipes 20 and 21 communicate with fittings and holes in cover 2 to which the hose connections 6 are joined. Double-walled heat exchanger 3 is made of two axially arranged and vertically positioned steel cylindrical shells 23 and 24, circular in horizontal section, with cylindrical shell 23 slightly larger than cylindrical shell 24. The area between the ends of the shells 23 and 24 are closed, thereby forming an annulus with which pipes 20 and 21 are in fluid communication. A heat exchanger fluid, usually a liquid and generally water, can be supplied to, and be removed from, the heat exchanger 3 by connections 6.

Silicone rubber tube 4 is spirally wound around the outer cylindrical shell 23 of the heat exchanger in such a manner that adjacent windings do not lie tightly together. The ends of tube 4 extend to connections 5 to which high pressure air hoses can be attached. Tube 4 constitutes a semi-permeable membrane through which gas can flow.

Stirring propeller 11 is mounted inside of the fermentation vessel on vertical shaft 10 which extends through bottom 7 to motor 9. The propeller is rotated at a speed of about 50 to 200 RPM selected to be adequate to achieve gentle macro-mixing of the fermenter culture liquid 12. The culture liquid and nutrients flow downwardly in the annular space 13 between cylinder 1 and shell 23 and become enriched with oxygen flowing through the walls of tube 4. The culture liquid 12 flows upwardly through sieve 14 and circulates around the small balls 15 on which the cells grow. By suitable sizing of sieve 14, the selection of the size and specific density of the balls 15, and by the speed of propeller 11, fluidization or suspension of the balls 15 can be achieved so that packing of the balls by settling is avoided. Fluidization of the balls eliminates static ball to ball, ball to sieve, and ball to heat exchanger contact which would create zones poor in nutrients and oxygen where cells could not live or grow, and would die.

Micro-mixing is achieved by flow of gas from the wall of spirally wound tube 4, and by the nonhomogeneous flow through the bed of balls 15. The circulation time of the liquid flow through the annular space 13 and through the bed of balls 15 can be adjusted so that the oxygen concentration within the bed of balls from the bottom to the top does not decrease enough to be considered.

When fermentation runs were carried out according to the invention, the bubbling in of air was completely avoided. Oxygen was supplied solely through the silicone tube spirally wound around the heat exchanger. The oxygen content of the culture liquid, measured continuously by means of an oxygen electrode, could be maintained uniform over several days when supplied in this manner. This indicated that the oxygen transfers from the flowing air in the silicone tube into the liquid nutrient medium and was always available in sufficient amount, even with increasing cell population and increasing culture volume. By increasing the flow rate of air in the silicone tube, or by increasing the air pressure, it is possible to increase oxygen transfer into the nutrient medium in the event the culture consumes increased amounts of oxygen.

By using the described method and apparatus, a constant increase of Mamestra brassicae cells could be achieved in cell culture suspensions of four and ten liters. It was possible for the first time, when compared to all previously used culture methods, to not only multiply cells but to also achieve a cell propagation of thirty times in a ten liter culture volume. Previously, the cell propagation increase was four to five times in culture volumes up to three liters. Furthermore, the cells produced according to the invention has an excellent morphological appearance, with at the most 10% of dead cells. In smaller prior art suspension cultures, such as of one to three liters, the percentage of dead cells often is substantially higher.

The use of tubes, hoses or similar hollow bands of oxygen permeable materials, such as silicone rubber, polytetrafluoroethylene (Teflon), or equivalently permeable material, permits oxygen enrichment of a nutrient medium to an extent which makes possible maximum propagation of insect cells in suspension volumes of ten liters or more. The cells are not prone to settle on, or attach to, the permeable tube 4 and thus do not slowly block oxygen flow, because the material of which the tubes are made provides a surface not suitable for cell adherence. For the same reason, cells do not adhere between the tube spirals, die there, decay and contaminate the nutrient medium with toxic decay products.

The following examples are presented to further illustrate the invention.

EXAMPLE 1

A suspension culture was started from the insect cell line IZD-Mb 0503 (IZD=Institute for Zoology Darmstadt; Mb=Mamestre brassicae=a type of butterfly; 0503=code number of the cell line; Lepidoptern-cell-line ATCC #CRL 8003) in a so-called spinner container, to which a standard liquid nutrient medium (pH 6.6) was added, with constant stirring by means of a magnetic stirrer. The nutrient medium used was published by T. D. Grace in Nature, 195, 788-789 (1962). The cells were permitted to multiply freely suspended in the nutrient medium. A starting population of $2 \times 10^5$ cells/ml of nutrient medium is necessary for multiplication. After three days, as a rule, a cell population of about 6 to $10 \times 10^5$ cells/ml is obtained. This is a population increase of 3 to 5 times the original amount. Because of nutrient depletion and "aging" of this culture, even with a longer fermentation time, a higher cell population cannot be achieved. This "parent culture" provides the cell preparation used to start a cell culture in a fermenter.

The oxygen and pH measuring electrodes of a fermenter like that shown in FIG. 1, were calibrated, autoclaved and recalibrated. After that they were inserted in the fermenter cover. A tube of silicone rubber having a 1.0 mm wall thickness was used as the membrane and wound on the heat exchanger. The cover (with the electrodes) and all parts of the fermenter which contact the cell suspension and the nutrient medium (same as above) flowing back and forth, as well as the systems supplying and removing the airstream, are sterilized in an autoclave.

The fermenter vessel was put together observing all conditions necessary to maintain the equipment sterile. The desired nutrient medium volume was filled through openings in the fermenter vessel cover provided for this purpose. Two liters of nutrient medium, to which cells were added to provide a population of $10^5$ cells/ml, were added to the 12 liter capacity fermenter vessel.

The fermenter was put into operation with stirring at 60 to 70 RPM, and a temperature of 28° C. in the suspension. The initial oxygen value (7.5 mg/l) and pH value were set via the measuring electrodes.

In the first 16 to 24 hrs. after the start of the cultivation, an oxygen enrichment of the nutrient was not absolutely necessary. However, oxygen enrichment is needed when the cell culture enters into its logarithmic growth phase and when the oxygen in the nutrient is used up due to the increase of the cell population and increased metabolism.

The oxygen is supplied via the silicone tube functioning as a permeable membrane through which oxygen from atmospheric air, or from an oxygen-air mixture, diffuses into the nutrient medium. To enrich the nutrient medium after the first 16 to 24 hrs., compressed air at a pressure of 0.5 to 1.0 atmosphere (gauge) was introduced via the silicone tube. If necessary, the pressure can be increased up to 2.0 atmospheres.

With an initial cell concentration of $10^5$ ml, the oxygen concentration decreases from 7.5 mg/l within 24 hours during the logarithmic cell increase (cell proliferation) to below 1% of the initial value. However, by means of oxygen (air) supplied through the silicone tube during the logarithmic cell increase, the oxygen concentration can be maintained at 10 to 30% of the initial concentration, which guarantees very good cell proliferation.

By means of the oxygen diffusion method according to the invention the number of cells per ml of nutrient medium was increased from $10^5$ up to 2 to $3 \times 10^6$ in four days.

After 2 to 3 days, maximum cell multiplication has been surpassed and the cell culture has entered the stationary phase in which the cells gradually stop dividing. Each ml then contains 2 to $3 \times 10^6$ cells. Then 6 to 7 liters of fresh nutrient medium was added under sterile conditions. The cell concentration was correspondingly reduced. The cells then change over from the stationary phase into a multiplying phase. After 2 to 3 days fermentation a cell concentration of 2 to $3 \times 10^6$ ml was again obtained. From the original $3 \times 10^8$ cells/3 liters, up to about $10^{11}$ cells have developed in a total volume of 10 liters.

Using the bubbling air method of the prior art, a volume increase of more than 4 liters would not have been possible. Four prior art cell propagations of 2.5 liters each would have resulted, at the most, in about $4 \times 10^9$ cells. The membrane method according to the invention yields a 20 times higher cell population.

About 5 liters of the cell suspension was removed from the 10 liter volume when the stationary phase was reached (2nd to 3rd day). Then 5 liters of fresh nutrient medium was added under sterile conditions to the fermenter. Thus, the remaining suspension was diluted and the cells, due to the new nutrient supply, again started their multiplying phase. Repetitions of these diluting-multiplying phases, when sterile conditions are maintained in the fermenter vessel, can be continued as long as permitted by the total condition of the cells. In stabilized cell lines, this can lead to a continuous operation.

EXAMPLE 2

The following cell lines can be fermented using the method described in example 1:

IZD-Mb 2006=Mamestra brassicae
IZD-Mb 1203=Mamestra brassicae
IZD-Mb 0504=Mamestra brassicae
IZD-Ld 1307=Lymantria dispar
IZD-Ld 1407=Lymantria dispar A multiplication rate, equally as good as with IZD-Mb 0503, can be expected for all of the listed insect cell lines. Other cell lines in addition to those just listed, which grow as suspension cultures, can be propagated or multiplied by the membrane oxygen diffusion method of the invention.

EXAMPLE 3

Recently it has become possible to propagate cells, not previously multipliable as a culture suspension, in a fermenter. Oxygen was supplied by bubbling air. By the use of so-called micro-carriers which are, as a rule, small balls having a diameter of less than 1 mm, cells that normally only grow on a solid base in the form of a cell "meadow" can be multiplied on the surface of balls. Polystyrene balls are particularly suitable.

About 5 g of the balls/liter of nutrient medium is introduced into a fermenter. That quantity of balls provides a surface of up to 30,000 cm². Tests with nondiploid Psylla (plant lice) cells in a suspension culture with micro-carrier balls have resulting in cell population figures of $4 \times 10^6$/ml of culture broth. Because high cell populations can result from the use of micro-carriers, the oxygen consumption is correspondingly high. With the air bubble method of the prior art the increased oxygen requirement is much harder to satisfy than with the membrane oxygen diffusion method according to the invention. With the membrane method, the metabolism efficiency of cells growing on the micro-carrier balls is improved, resulting in faster and increased cell division. The cell population increases faster per unit of time so that fermenter preparations from micro-carrier cultures supply more cells.

The foregoing detailed description has been given for clearness of understanding only, and no unnecessary limitations should be understood therefrom, as modifications will be obvious to those skilled in the art.

What is claimed is:

1. In a fermentation vessel for propagating animal cells in suspension cultures and monolayer cultures in which oxygen must be supplied to the cells in a liquid nutrient medium in the vessel for cell metabolism and multiplication, the improvement comprising a permeable membrane partially defining a chamber or volume in the fermentation vessel and made of a polymeric material on which the cells do not grow to a significant extent but through which oxygen can diffuse directly, without bubbling, into at least a 4 liter volume of the liquid nutrient medium containing the cells;
   the membrane being of a size and shape so that a sufficient amount of oxygen is diffused into the liquid so as to enable cell propagation;
   conduit means communicating with the chamber from outside the vessel for supplying oxygen to the chamber for diffusion through the membrane; and
   mechanical liquid-agitation means located within the fermentation vessel.

2. An improved fermentation vessel according to claim 1 in which the polymeric material is silicone rubber or polytetrafluoroethylene.

3. An improved fermentation vessel according to claim 1 in which the membrane is a tube.

4. An improved fermentation vessel according to claim 3 in which the tube wall is about 0.6 to 1.2 mm thick.

5. An improved fermentation vessel according to claim 3 in which the tube is on a rigid support.

6. An improved fermentation vessel according to claim 5 in which the rigid support is a heat exchanger.

7. A method comprising growing animal cells in suspension cultures and monolayer cultures in a fermentation vessel containing at least a 4 liter volume of a liquid nutrient medium, and supplying the cells with oxygen through a permeable membrane partially defining a chamber or volume in the fermentation vessel and made of a polymeric material on which almost no cell growth takes place, so that the oxygen diffuses directly without bubbling into the liquid medium;
   the oxygen being supplied to the chamber from outside the vessel; and
   the membrane being of a size and shape so that a sufficient amount of oxygen is diffused into the liquid so as to enable cell propagation.

8. A method according to claim 7 in which the membrane is in the form of a tube.

9. A method according to claim 8 in which the tube has a wall thickness of about 0.6 to 1.2 mm.

10. A method according to claim 8 in which the tube is silicone rubber.

11. A method according to claim 7 in which the membrane is a tube spirally wound on a rigid support.

12. A method according to claim 11 in which the rigid support is a heat exchanger.

13. A method according to claim 7 in which the animal cells are from a non-vertebrate.

14. A method according to claim 13 in which the animal cells are insect cells.

15. A method according to claim 7 in which cell growth continues until cell multiplication increases the cell population to at least 20 times the cell population at the start of fermentation.

16. A method according to claim 7 in which the polymeric material is silicone rubber or polytetrafluoroethylene.

* * * * *